(12) United States Patent
Caufriez et al.

(10) Patent No.: US 9,084,797 B2
(45) Date of Patent: Jul. 21, 2015

(54) PROGESTERONE TREATMENT FOR IMPROVING SLEEP QUALITY

(75) Inventors: Anne Caufriez, Brussels (BE); Georges Copinschi, Brussels (BE)

(73) Assignee: BESINS HEALTHCARE LUXEMBOURG SARL, Luxembourg (LU)

( * ) Notice: Subject to any disclaimer, the term of this patent is extended or adjusted under 35 U.S.C. 154(b) by 0 days.

(21) Appl. No.: 13/469,296

(22) Filed: May 11, 2012

(65) Prior Publication Data

US 2012/0302535 A1 Nov. 29, 2012

Related U.S. Application Data

(60) Provisional application No. 61/489,066, filed on May 23, 2011.

(51) Int. Cl.
*A61K 31/57* (2006.01)
*A61P 25/00* (2006.01)

(52) U.S. Cl.
CPC ..................... *A61K 31/57* (2013.01)

(58) Field of Classification Search
USPC ....................................................... 514/177
See application file for complete search history.

(56) References Cited

FOREIGN PATENT DOCUMENTS

WO  WO 2006/128057  * 11/2006

OTHER PUBLICATIONS

Montplaisir et at (Sleep in menopause: differential effects of two forms of hormone repleacement therapy, Journal of the North American Menopause Society, vol. 8, No. 1, pp. 10-16).*
Caufriez et al., "Impact of Progesterone Administration on Sleep Quality, GH and TSH in Postmenopausal Women," Endocrine Reviews, Supplement 1, vol. 31, No. 3, p. S1312, Jun. 19-22, 2010 (Abstract).
Caufriez et al., "Progesterone Prevents Sleep Disturbances and Modulates GH, TSH, and Melatonin Secretion in Postmenopausal Women," J. Clin. Endocrinol. Metab., vol. 96, No. 4, Apr. 2011.
Schüssler et al., "Progesterone reduces wakefulness in sleep EEG and has no effect on cognition in healthy postmenopausal women," Psychoneuroendocrinology, vol. 33, pp. 1124-1131, 2008.
Friess et al., "Progesterone-induced changes in sleep in male subjects," Am. J. Physiol, vol. 272, pp. E885-E891, 1997.
Henrich et al., "Investigating the Effects of Estradiol or Estradiol/Progesterone Treatment on Mood, Depressive Symptoms, Menopausal Symptoms and Subjective Sleep Quality in Older Healthy Hysterictomized Women: A Questionnaire Study," Neuropsychobiology, vol. 52, pp. 17-23, 2005.
Copinschi et al., "Sleep and Hormonal Changes in Aging," Endocrinol. Metab. Clin. N Am, vol. 42, pp. 371-389 2013.
Lancel et al., "γ-Aminobutyric Acid$_A$ (GABA$_A$) Agonist 4,5,6,7-Tetrahydroisoxazolo[4,5-c]pyridine-3-ol Persistently Increases Sleep Maintenance and Intensity during Chronic Administration to Rats," The Journal of Pharmcology and Experimental Therapeutics, vol. 293, No. 3, 2000.

* cited by examiner

*Primary Examiner* — Kathrien Cruz
(74) *Attorney, Agent, or Firm* — Foley & Lardner LLP

(57) ABSTRACT

Described herein are therapeutic methods using progesterone and progesterone analogs to improve sleep quality. The methods may be particularly useful to treat subject with perturbed sleep patterns, such as subjects who suffer from mid-sleep period awakenings.

16 Claims, 4 Drawing Sheets

Night 1: no catheter
no blood sampling

Night 2: iv catheter
24-h blood sampling

Night 1: no catheter no blood sampling

Night 2: iv catheter 24-h blood sampling

SLOW-WAVE SLEEP (min)
Friedman test: $P=0.03$

REM SLEEP (min)
Friedman test: $P=0.26$

☐ Night 1: no catheter
no blood sampling

■ Night 2: iv catheter
24-h blood sampling

SLOW-WAVE ACTIVITY (mV$^2$)
Friedman test: $P = 0.004$

REM LATENCY (min)
Friedman test: $P = 0.21$

☐ Night 1: no catheter
no blood sampling

■ Night 2: iv catheter
24-h blood sampling

PROGESTERONE TREATMENT FOR IMPROVING SLEEP QUALITY

FIELD OF THE INVENTION

Described herein are therapeutic methods using progesterone and progesterone analogs to improve sleep quality. The methods may be particularly useful to treat subject with perturbed sleep patterns, such as subjects who suffer from mid-sleep period awakenings.

BACKGROUND

In mammals, sleep is divided into two broad types: rapid eye movement (REM) and non-rapid eye movement (NREM or non-REM) sleep. The American Academy of Sleep Medicine (AASM) further divides NREM into three stages: N1, N2, and N3, the last of which is also called delta sleep or slow-wave sleep (SWS). (see, e.g. Silber M H, et al., 2007, *J. of Clin. Sleep Med.*, 3 (2): 121-31). This revised scoring introduced in 2007 combined the former stage III and stage IV (referred to in the Example hereinbelow) into the new stage N3.

Sleep proceeds in cycles of REM and NREM, the order normally being N1→N2→N3→N2→REM. There is a greater amount of deep sleep (stage N3) earlier in the sleep cycle, while the proportion of REM sleep increases later in the sleep cycle and just before natural awakening. In humans, each sleep cycle lasts on average from 90 to 110 minutes.

Stage N1 refers to the transition of the brain from alpha waves having a frequency of 8-13 Hz (common in the awake state) to theta waves having a frequency of 4-7 Hz. This stage is sometimes referred to as somnolence or drowsy sleep. Sudden twitches and hypnic jerks, also known as positive myoclonus, may be associated with the onset of sleep during N1. Some people may also experience hypnagogic hallucinations during this stage. During N1, the subject loses some muscle tone and most conscious awareness of the external environment.

Stage N2 is characterized by sleep spindles ranging from 11-16 Hz (most commonly 12-14 Hz) and K-complexes. During this stage, muscular activity as measured by EMG decreases, and conscious awareness of the external environment disappears. This stage occupies 45-55% of total sleep in adults.

Stage N3 (deep or slow-wave sleep) is characterized by the presence of a minimum of 20% delta waves ranging from 0.5-2 Hz and having a peak-to-peak amplitude >75 µV. This is the stage in which parasomnias such as night terrors, nocturnal enuresis, sleepwalking, and somniloquy occur. Many illustrations and descriptions still show a stage III with 20-50% delta waves and a stage IV with greater than 50% delta waves; these have been combined as stage N3.

Rapid eye movement sleep, or REM sleep, accounts for 20-25% of total sleep time in most human adults. The criteria for REM sleep include rapid eye movements as well as a rapid low-voltage EEG. Most memorable dreaming occurs in this stage. At least in mammals, a descending muscular atonia is seen. Such paralysis may be necessary to protect organisms from self-damage through physically acting out scenes from the often-vivid dreams that occur during this stage.

In older adults, sleep is disturbed with more awakenings, less SWS and less REM sleep. The older population also is the primary user of hypnotics (see, e.g., Mendelson, *Human Sleep: Research and Clinical Care*, Plenum Press, New York, p. 436, 1987), although it is widely accepted that chronic hypnotic use has generally deleterious effects (see, e.g., Prinz, *J. Clin. Neurophysiol.*, 12:139-146, 1995).

Commercially available hypnotics, including the benzodiazepines, improve sleep efficiency but do not consistently increase either SWS or REM sleep. See, e.g., Gaillard, in *Principles And Practice of Sleep Medicine*, Kryger, Roth, Dement (eds), W.B. Saunders, Philadelphia, Pa., p. 349-354, 1994.

Hypnotics (e.g., benzodiazepines and Z-compounds) act on sleep efficiency, but do not improve, but rather tend to worsen, sleep patterns. Thus these drugs may be useful for patients showing troubles going to sleep, i.e., falling asleep. Because of their modification of the sleep pattern however, they do not prove particularly useful for patients who have no problems going to sleep, but who wake up during the night, e.g., suffer from mid-sleep period awakenings.

Thus, there remains a need for effective treatments for perturbed sleep patterns.

The effects of progesterone on sleep have been studied by a number of groups, and their results tend to diverge. In 1997, Friess et al., Am. J. Physiol., 1997, 272: E885-91, reported an effect on sleep patterns in men orally administered 300 mg progesterone, akin to those induced by agonistic modulators of the GABA(A) receptors complex, and especially in its modification of the sleep pattern: increase of stage N2 time and decrease of stage N3 time and of REM sleep. In 2005, Heinrich and Wolf, *Neuropsychobiology*, 2005, 52:17-23, reported results of a questionnaire-based study that found that estradiol and progesterone had no effect on subjective sleep quality in hysterectomized women administered 2 mg estradiol valerate and 100 mg progesterone. In 2008, Schüssler et al., *Psychoneuroendocrinology*, 2008, 33:1124-1131, reported a decrease of intermittent time spent awake and increase in REM sleep in the first third of the night in post-menopausal women administered 300 mg progesterone; however, there were no significant differences between baseline, placebo and progesterone in the total duration of REM. Stage 2 or SWS, or in the absolute power spectra delta, theta, sigma, alpha and beta.

SUMMARY

In some embodiments, there are provide methods for improving sleep quality in a subject in need thereof, comprising administering a therapeutically effective amount of progesterone to the subject. In some embodiments, the subject suffers from or is as at risk of a perturbed sleep pattern. In some embodiments, the subject suffers from mid-sleep period awakening. In some embodiments, the subject has been diagnosed with a sleep disorder. In some embodiments, the subject is a female who suffers from perturbed sleep patterns due to menopause. In some embodiments, subject is subject to environment-related sleep perturbations such that the subject suffers from or is at risk of perturbed sleep patterns due to an extraneous cause, such as an intravenous infusion line, an intravenous catheter, and other indwelling medical devices. In some embodiments, the subject is not taking or being administered estrogen.

In some embodiments, the method comprises once daily administration of progesterone. In some embodiments, the progesterone is administered within one hour prior to the subject retiring. In some embodiments, the method comprises once daily administration of progesterone over a period of time of at least 7 days, or at least 30 days.

In some embodiments, the therapeutically effective amount of progesterone is from 200 mg to 500 mg daily, such as from 300 mg to 400 mg daily.

In some embodiments, the progesterone is administered orally.

In some embodiments, the progesterone is provided in a pharmaceutical composition in the form of a soft capsule comprising micronized progesterone solubilized in an edible oil, such as peanut, sunflower, olive, almond, sesame and colza oils.

In some embodiments, the method is effective to improve sleep quality as measured by one or more of a decrease in wake time, increase in SWS and/or REM sleep, increase in sleep maintenance, increase in sleep efficiency, decrease in sleep latency and/or normalization of distribution of SW and REM stages during the sleep period.

DETAILED DESCRIPTION

Figure 1A:
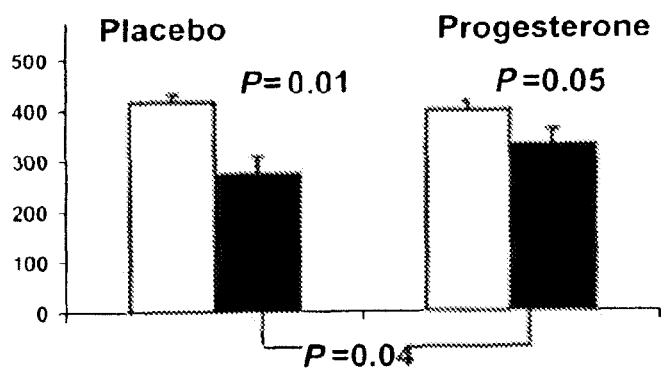
FIGS. 1A-1D illustrate the results of the clinical trial reported in example 1, and show that the administration of progesterone improves sleep quality.
Figure 1A:
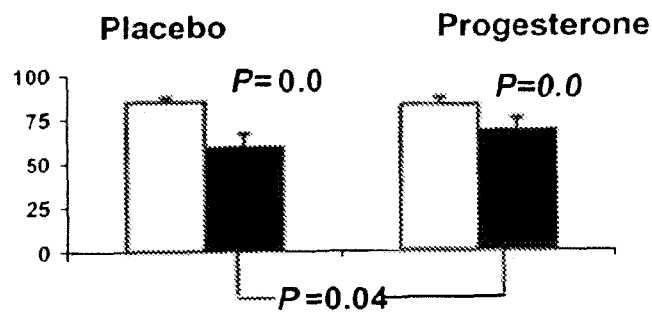
Figure 1A:
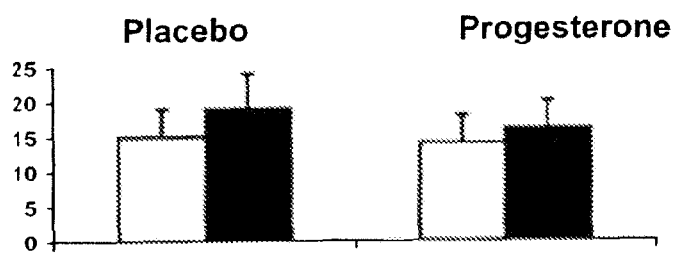
Figure 1A:
Figure 1A:

In surprising contrast with the current state of the art, the present inventors have found that progesterone is capable of improving sleep architecture (e.g., sleep quality) in patients with a perturbed sleep architecture, such as subjects who suffer from mid-sleep period awakenings. These effects of progesterone on sleep architecture are very different from the effects of conventional hypnotics, which induce artificial sleepiness but do not generally impact overall sleep architecture or address the problem of mid-sleep period awakenings. Thus, described herein are methods of improving sleep quality in subjects having disturbed sleep patterns comprising administering progesterone to the subjects.

Definitions

Technical and scientific terms used herein have the meanings commonly understood by one of ordinary skill in the art to which the present invention pertains, unless otherwise defined. Reference is made herein to various methodologies known to those of ordinary skill in the art. Any suitable materials and/or methods known to those of ordinary skill in the art can be utilized in carrying out the present invention. However, specific materials and methods are described.

As used herein, the singular forms "a," "an," and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent depending on the context in which it is used. If there are uses of the term which are not clear to persons of ordinary skill in the art given the context in which it is used, "about" will mean up to plus or minus 10% of the particular term.

As used herein, the phrase "therapeutically effective amount" means that drug dosage that provides the specific pharmacological response for which the drug is administered in a subject in need of such treatment. It is emphasized that a therapeutically effective amount or therapeutic level of a drug will not always be effective in treating the conditions/diseases described herein, even though such dosage is deemed to be a therapeutically effective amount by those of skill in the art. For convenience only, exemplary dosages, drug delivery amounts, therapeutically effective amounts and therapeutic levels are provided herein with reference to adult human subjects. Those skilled in the art can adjust such amounts in accordance with standard practices as needed to treat a specific subject and/or condition/disease.

As used herein, "sleep pattern" or "sleep architecture" refer, for a given individual, to the time spent in each of the sleep stages (e.g., REM, N1, N2 and N3, or, alternatively, REM, Stage I, Stage II, Stage III and Stage IV), including the relative proportion of the duration of each stage as compared to the duration of other stages. Parameters of "normal" sleep patterns or sleep architecture for specific populations (e.g., postmenopausal women) are known in the art. See, e.g., Latta et al., 2005, Sleep, 28:1525-1534; Sahlin et al., 2009, Sleep Med., 10:1025-1030.

A subject in need of improvement of sleep architecture or sleep quality may exhibit sleep patterns that deviate from "normal" sleep patterns in one or more parameters, may suffer from or be at risk of perturbed sleep patterns, or may be diagnosed with a sleep disorder. In specific embodiments, the subject suffers from mid-sleep period awakenings, even if the subject does have problems falling asleep.

In determining whether a drug or treatment protocol achieves improvement of sleep architecture or sleep quality, a number of different parameters may be considered. For example, one or more of a decrease in wake time, increase in SW and/or REM sleep, increase in sleep maintenance, increase in sleep efficiency, decrease in sleep latency and/or normalization of distribution of SW and REM stages during sleep, may be considered to be improvements in sleep quality or sleep architecture. The methods by which one can determine improvement in sleep quality are known in the art and illustrated in the example. A drug or treatment protocol offering improvements in any one or more of these parameters to a subject would be considered to have improved the sleep quality or sleep architecture of that subject.

Progesterone & Progesterone Analogs

In some embodiments, the methods comprise administering progesterone. In other embodiments, the methods comprise administering a progesterone analog. In some embodiments the progesterone analog interacts with the GABA system, such as by binding to GABA receptors. In some embodiments, the progesterone analog is a CNS metabolite of progesterone. In specific embodiments, the progesterone analog is selected from the group consisting of pregnanolone, allopregnanolone and androstanediol.

The term "progesterone" as used herein refers to a member of the progestogen family having the structure of Formula I below:

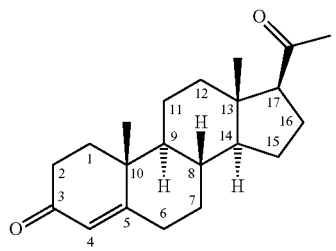

Formula I

Progesterone is also known as D4-pregnene-3,20-dione; delta-4-pregnene-3,20-dione; or pregn-4-ene-3,20-dione. In specific embodiments, the progesterone is micronized. Proquina (Mexico) is one supplier of micronized progesterone.

For convenience, the methods are described herein with reference to "progesterone." It should be understood, however, that any suitable progestogen as described herein can be used without going beyond the scope of the invention.

Methods

As noted above, described herein are methods of improving sleep quality in subjects having disturbed sleep patterns comprising administering a progestogen, such as progesterone, to the subject. As noted above, it has now been surprisingly found that progesterone does not act as a conventional hypnotic, which induces artificial sleepiness, but it acts as a physiologic regulator. Moreover, it improves sleep quality, while currently available hypnotics (benzodiazepines and Z-drugs) tend to inhibit, rather than enhance, slow-wave activity (see, e.g., Dijk, *World J. Biol. Psychiatry*, 11:22-28).

In some embodiments, the method comprises administering a therapeutically effective amount of a progestogen, such as progesterone, to a subject just prior to that subject retiring (e.g., going to sleep). In some embodiments, the administering occurs within about one hour prior to retiring, but the methods include administrations that occur one-half hour or less prior to retiring.

In some embodiments, the methods further comprise administering a second, third, or fourth dose of progesterone during the normal sleep period. In some embodiments, a further dose of progesterone is administered if the subject experiences awakening during the intended sleep period.

In some embodiments, the progesterone is administered in a pharmaceutical composition, such as pharmaceutical composition as described in more detail below.

In specific embodiments, the methods involve administering the pharmaceutical composition in a single oral dose formulation (e.g., a "unit dose") about one-half hour before retiring. The term "unit dose" refers to a physically discrete unit of a dosage form suitable for use in humans, each unit containing a predetermined quantity of the pharmaceutical composition calculated to provide a therapeutically effective amount, e.g., to produce the desired therapeutic effect. The unit dose may be formulated in a pharmaceutically acceptable carrier for the route of administration in a dose appropriate for the selected treatment regimen.

In general, a specific therapeutically effective amount for a given subject will be determined by the practitioner, and may be particular to each individual. For example, the weight of the subject and/or the subject's specific sleep disturbance and/or extent thereof may influence the amount of progestogen (e.g., progesterone) administered. For example, subjects having a greater or lesser perturbation of sleep pattern may be administered greater or lesser amounts, respectively, of the progestogen (e.g., progesterone).

Exemplary doses range from about 200 mg to about 500 mg per day progesterone, or equivalent amount of another progestogen. In another embodiment, the daily dose of drug is from 200 to 500 mg, or from 250 mg to 450 mg, or from 300 to 400 mg. In specific embodiments, the daily dose is about 200 mg, about 300 mg, or about 400 mg progesterone, such as 200 mg, 300 mg, or 400 mg progesterone. In a specific embodiment, the daily dose is 300 mg progesterone.

In some embodiments, the method comprises a chronic dosage regimen. As used herein, a "chronic dosage regimen" refers to daily administration for a period of at least 7 days, at least 10 days, at least 14 days, at least 15 days, at least 20 days, at least 21 days, or at least 30 days.

The methods described herein are effective to improve sleep quality or sleep architecture as measured by one or more of a decrease in wake time, increase in SWS and/or REM sleep, increase in sleep maintenance, increase in sleep efficiency, decrease in sleep latency and/or normalization of distribution of SW and REM stages during the sleep period.

In some embodiments, the methods include treating subjects presenting with a perturbed sleep pattern. In some embodiments, the subject has been diagnosed or determined to suffer from a perturbed sleep pattern or sleep disorder. In particular embodiments, the subject generally have no trouble going to sleep, but suffer from mid-sleep period awakenings (e.g., wake up in the middle of the night).

In some embodiments, the subject is a female presenting with perturbed sleep patterns due to menopause.

In other embodiments, the subject is subject to environment-related sleep perturbations, such that the subject presents (or is at risk for) perturbed sleep patterns due to an extraneous cause, such as the presence of an intravenous infusion line, intravenous catheter, or other indwelling medical device.

In some embodiments, the subjects are over 40, over 50, over 60, or over 70 years old.

In some embodiments, the subjects are female. In other embodiments, the subjects are male.

In some embodiments, the method does not include the administration of estrogen. In some embodiments, the subject is not taking or being administered estrogen.

Pharmaceutical Compositions

The methods include administration of the progestogen via any route of administration, including oral, nasal, buccal, rectal, vaginal, topical, intradermal, subcutaneous, intramuscular, intraperitoneal, or intravenous infusion or injection.

In some embodiments, the method comprises oral administration of the progestogen.

The progestogen may be administered in any pharmaceutical form which is suited to deliver a therapeutically effective amount to achieve therapeutic systemic levels, as discussed above.

In specific embodiments, the progesterone is micronized.

In some embodiments, the method comprises administering progesterone in a composition that comprises progesterone solubilized in an edible oil, such as a composition comprising micronized progesterone solubilized in an edible oil. In specific embodiments, the pharmaceutical composition further comprises soya bean lecithin. In specific embodiments, the edible oil is selected from the group consisting of peanut, sunflower, olive, almond, sesame and colza oils, such as being sunflower oil or olive oil.

As used herein, the term "micronized progesterone" means a progesterone in which at least about 80% of the particles have a particle size of between 1 and 15 microns. In specific embodiments, at least about 50% of the particles have a particle size of between 1 and 10 microns. In further specific embodiments, at least about 25% of the particles have a particle size of between 1 and 5 microns. As used herein, these particle sizes can be measured using a laser particle sizer of the Malvern type, by the procedure described in the examples of U.S. Pat. No. 7,431,941, the entire contents of which are incorporated herein by reference.

In specific embodiments, the composition is one as described in U.S. Pat. No. 7,431,941, the entire contents of which are incorporated herein by reference.

According some embodiments, the pharmaceutical composition has a progesterone/oil(s) ratio between 0.15/1 and 3/1, such as between 0.25/1 and 2/1, including between 0.40/1 and 1/1, such as 0.67/1.

According to some embodiments, the pharmaceutical composition has a soya bean lecithin/oil(s) ratio between 0.0005/1 and 0.03/1, such as between 0.001/1 and 0.02/1, including between 0.004/1 and 0.01/1, such as 0.0067/1.

Such pharmaceutical compositions may be in the form of, inter alia, a soft capsule, a hard capsule, a tablet, a drinkable suspension. In specific embodiments, the composition is provided in a capsule that comprises gelatin or an equivalent.

Such pharmaceutical compositions may be administered orally or vaginally. Vaginal administration represents an alternative to oral administration in the case of side effects due to oral progesterone or of contraindication to oral administration (hepatopathy).

In some embodiments, a unit dose of the pharmaceutical composition comprises between 2 mg and 800 mg of micronized progesterone, between 100 mg and 400 mg micronized progesterone, 200 mg, 300 mg, or 400 mg micronized progesterone, or about 300 mg micronized progesterone, such as 300 mg micronized progesterone.

In specific embodiments, the pharmaceutical composition is provided as a soft gelatine capsule containing the following ingredients: micronized progesterone, sunflower oil and soya bean lecithin. The components may be present according to the following ratios (defining an exemplary pharmaceutical unit comprising 100 mg progesterone):

| | |
|---|---|
| Progesterone | 100 mg |
| Oil | 149 mg |
| Soya Bean Lecithin | 1 mg |

The following example is included as illustrative only. This example is in no way intended to limit the scope of the invention. Other aspects of the invention will be apparent to those skilled in the art to which the invention pertains.

EXAMPLE

Prevention of Sleep Disturbances in Postmenopausal Women

Subjects: Eight postmenopausal women, aged 48-74 yr (mean 57.4 yr), were selected after a careful clinical and biological evaluation. Investigations were performed 2-17 years (mean: 8.0 years) after natural menopause (seven subjects) or bilateral ovariectomy (one subject). Mean age at menopause was 49.4 years (range: 41-57 yr). Three subjects had never received hormone replacement therapy, and five subjects had been off such treatment for 2-6 months (mean: 4.4 months) at the time of enrollment. Body weight was in the normal range for all (mean+/−SEM of body mass index 22.1+/−0.8 kg/m2). In all subjects, estradiol plasma levels were <10 ng/liter. FSH plasma levels averaged 90 IU/liter (range: 66-136 IU/liter).

Smokers, shift workers, subjects who had travelled across time zones during the last 2 months, individuals with a personal history of drug abuse or with personal or family history of psychiatric, neurological, endocrine, or metabolic disorders, and subjects with current vasomotor symptoms, dieting, or intensive physical exercise were excluded from the study.

Each subject was examined and had to answer a battery of specific questions concerning her sleep habits. To be included in the study, subjects had to comply with the following requirements: regular sleep schedules (bedtimes from 2200-2400 h to 0600-0800 h), no difficulty falling asleep, no complaints of awakenings during the sleep period, no snoring, no periodic limb movements, and no daytime fatigue or sleepiness.

Experimental Protocol: The protocol was designed as a randomized, double-blind, placebo-controlled study.

Before the beginning of the investigation, subjects spent two consecutive nights in the sleep laboratory to habituate to the sleep laboratory environment and recording procedures. On both nights, electrodes for polygraphic sleep recordings were placed around 2230 h. Polygraphic sleep recordings were obtained during the second night.

Thereafter, all subjects participated in random order in two studies (referred to as placebo and progesterone), separated from each other by at least 1 month. The placebo study preceded the progesterone study in four subjects and followed the progesterone study in the other four volunteers.

Each study included an initial 20 day ambulatory period. During this period, the subjects were asked to maintain regular sleep-wake cycles (bedtime 2300-0700 h in darkness) and meal schedules (0800 h, 1230 h, 1900 h), They took daily, at 2300 h, a capsule of either 300 mg of progesterone or placebo.

At the end of the ambulatory period, they were admitted at about 1600 h to the sleep laboratory for 44 hours. During hospitalization, subjects were maintained in a seated/upright position in normal indoor light conditions (+/−300 lux), and no naps were allowed during the scheduled wake periods (0700-2300 h). Meals were served at 0800 h, 1230 h, and 1900 h. At 2300 h, they received their usual capsule of either 300 mg of progesterone or placebo. During both scheduled sleep periods (2300-0700 h), subjects were kept recumbent in total darkness and sleep was polygraphically recorded.

On the morning after the first night, a sterile heparin-lock catheter was inserted intravenously in the forearm and blood samples were collected for 24 hours at 15-minute intervals. The iv line was kept permeable by a slow drip of heparinized saline. During the sleep period, the indwelling catheter was connected to plastic tubing extending to an adjacent room and blood samples were collected remotely, as previously described (Leproult et al., 2005, Clin. Endocrinol. 63: 298-304). The total amount of blood withdrawn was less than 300 ml for each inpatient study. The subjects were discharged at about 1200 h after the second night.

Sleep Analysis: Polygraphic sleep recordings were visually scored at 30 second intervals, using standardized criteria (Rechtschaffen and Kales, 1968, Los Angeles: UCLA Brain Information Service/Brain Research Institute) by the same experienced scorer who was blind to the clinical condition of the subject.

Sleep onset and morning awakening were defined as, respectively, the times of the first and last 30 second intervals scored II, III, IV, or rapid eye movement (REM).

The sleep period was defined as the time interval separating sleep onset and final awakening.

Total sleep time was defined as the sleep period minus the total duration of wake after sleep onset (WASO).

Sleep latency was defined as the time interval from lights off until sleep onset.

Sleep efficiency was calculated as the total sleep time, expressed as percentage of the time allocated to sleep.

Slow-wave sleep (SWS) was defined as stages III+IV.

A spectral analysis was performed on the central electroencephalogram lead (PRANA, Philools, Strasbourg, France) (Latta et al., 2005, *Sleep* 28: 1525-1534).

Muscular, ocular, and movement artifacts were eliminated before spectral analysis.

Delta activity was calculated as the absolute spectral power in the frequency band 0.5-4 Hz. Mean delta power was calculated per 30-sec epoch. Delta power in non-REM sleep quantifies slow-wave activity (SWA) (i.e., the intensity of SWS).

Statistical Tests: Nonparametric tests (Friedman test, Wilcoxon signed rank test, Spearman rank test) were used for statistical calculations (StatView SE+software for Macintosh computers, Abacus Concepts Inc., Berkeley, Calif.). Detection of outliers was performed by the Grubbs test (Grubbs, 1969, *Technometrics* 11:1-21; Grubbs and Beck, 1972, *Technometrics* 14:847-854). All group values are expressed as the mean+/−SEM.

Figure 1B:
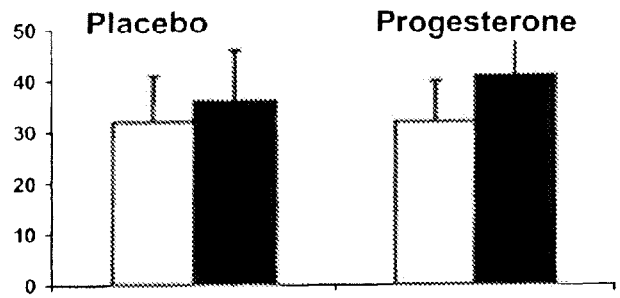
Figure 1B:
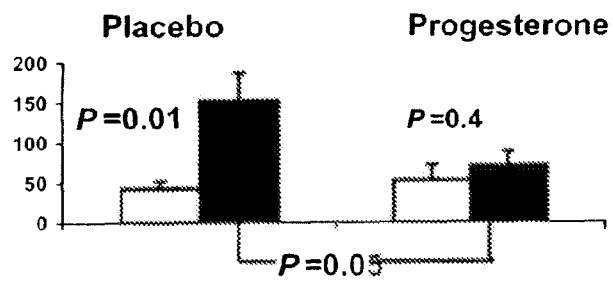
Figure 1B:
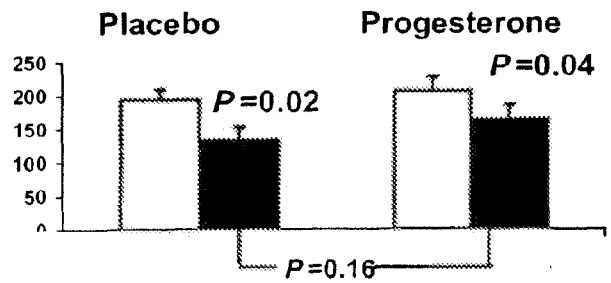
Figure 1B:
Figure 1B:
Figure 1C:
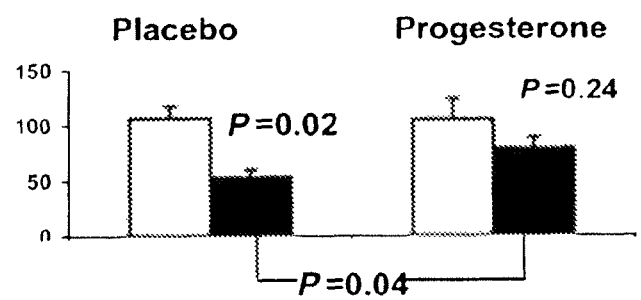
Figure 1C:
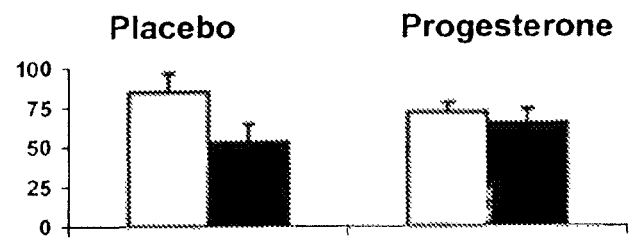
Figure 1D:
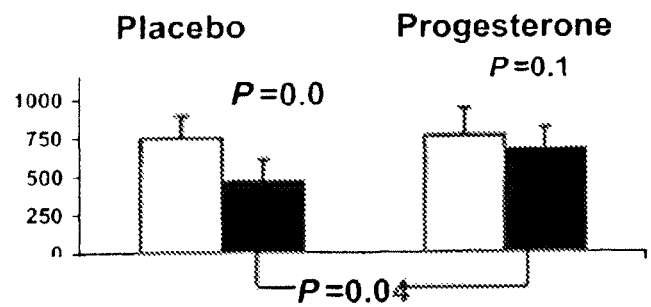
Figure 1D:
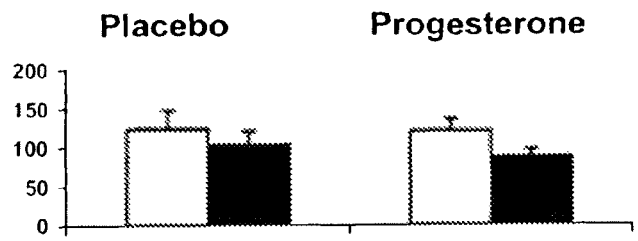

Results:

Sleep (FIGS. 1A-1D): During night 1 (without catheter), sleep duration (averaging nearly 7 hours) and architecture were in the normal range for this population of postmenopausal women (Latta et al., 2005, *Sleep*, 28:1525-1534, Sahlin et al., 2009, *Sleep Med.*, 10:1025-1030). There were no differences between placebo and progesterone treatment (P >=0.33).

The effects on sleep of the blood sampling procedure (which included the presence of an iv catheter) were quite different under placebo versus under progesterone.

Under placebo, all sleep variables, except stage I, sleep latency, and REM latency, were considerably disturbed during night 2, compared with night 1 (P<=0.02): mean WASO duration was increased by more than 250% (from 43+/−9 min to 152+/−35 min), and dramatic decreases were observed in total sleep time (almost 30%), sleep efficiency (35%), the duration of stage II (more than 30%), SWS duration (almost 45%), and total SWA (almost 40%). The decrease in REM sleep averaged almost 40% (Friedman test, not significant).

In contrast, only minor alterations were observed under progesterone treatment: total sleep time (P=0.05), sleep efficiency (P=0.07), and stage II (P=0.04) decreased by about 20%. Other sleep variables were not significantly altered. The disturbances in sleep duration and quality observed under placebo during night 2 (with catheter) were considerably reduced under progesterone treatment. Indeed, under progesterone compared with placebo, mean WASO duration was more than 50% lower (P=0.05), total sleep time was 20% higher (P=0.04), sleep efficiency 15% higher (P=0.04), and total SWA more than 40% higher (P=0.04).

SWS was similar under placebo (69+/−16 min) and progesterone (84+/−10 min), but this apparent similarity was attributable to an outlier (P<0.01). SWS duration under placebo was 175 min in this outlier, vs. values ranging from 36 to 86 min in the other seven subjects. If this outlier was excluded from the analysis, SWS averaged 53+/−7 min and 79+/−10 min under placebo and progesterone, respectively (P=0.04).

There were no differences in sleep latency, stage I, stage II, REM sleep, and REM latency.

Hormone Levels: Levels of growth hormone (GH) and thyroid-stimulating hormone (TSH) also were assessed. Over the scheduled sleep period (2300-0700 h) mean (+/−SEM) GH secretion was enhanced under progesterone treatment (154+/−44 µg vs. 103+/−25 µg, P=0.05), while over the scheduled wake period (0700-2300 h) it was similar under both conditions (239+/−91 µg vs. 241+/−90 µg, P=0.05). IGF-I levels (measured on 2-3 morning plasma samples) tended to increase under progesterone (103+/−23 µg/l vs. 90+/−20 µg/l, P=0.09). Conversely, 24 hour TSH levels tended to decrease under progesterone (0.91+/−0.13 mU/l vs. 1.19+/−0.22 mU/l, P=0.07), while 24 hour free T4 levels were similar (10.3+/−0.4 ng/l vs. 10.1+/−0.4 ng/l, P=0.53). Under both conditions, relatively stable daytime TSH levels were followed by the expected circadian evening rise (onset at 2000 h+/−24 min vs. 2038 h+/−23 min, P=0.23), but the sleep-related inhibition of TSH secretion occurred earlier under progesterone: over the 2300-0100 period, a significant negative slope of the linterar regression of TSH values was evident under progesterone (P=0.05) but not under placebo (P=0.12), resulting in significantly lower TSH levels under progesterone over the 2300-0700 period (0.98+/−0.18 mU/l vs. 1.39+/−0.24 mU/l, P=0.05).

Conclusion: During the laboratory session, sleep duration and architecture during night 1 (without catheter) were normal and progesterone administration had no effect. Consistent with the findings previously reported in healthy older women (Latta et al., 2005, *Sleep*, 28:1525-1534, Vitiello et al., 1996, *Sleep*, 19:304-311), sleep profiles under placebo were markedly disrupted during night 2 by the indwelling iv catheter and the blood sampling procedure. In contrast, those sleep alterations were largely prevented by the administration of progesterone.

Thus, progesterone administration had no effect on normal sleep, but dramatically improved sleep that was subject to environment-related sleep perturbations. Notably the administration of progesterone improved both sleep duration and sleep quality (shown in particular by increases in SWS and SWA).

Thus, the example indicates that methods comprising administering progesterone may improve sleep quality or sleep architecture in post-menopausal women whose sleep is disturbed by environmental conditions.

Additionally, the administration of progesterone modulates GET and TSH secretion.

What is claimed is:

1. A method for improving sleep quality in a subject that is subject to an environment-related sleep perturbation selected from the group consisting of an intravenous infusion line, an intravenous catheter, and other indwelling medical devices, comprising administering a therapeutically effective amount of progesterone to the subject, wherein the improved sleep quality comprises an increase in slow-wave sleep.

2. The method of claim 1, wherein the subject suffers from or is as at risk of a perturbed sleep pattern.

3. The method of claim 1, wherein the subject suffers from mid-sleep period awakening.

4. The method of claim 1, wherein the subject has been diagnosed with a sleep disorder.

5. The method of claim 1, wherein the subject is a female who suffers from perturbed sleep patterns due to menopause.

6. The method of claim 1, wherein the subject is not taking or being administered estrogen.

7. The method of claim 1, wherein the method comprises once daily administration of progesterone.

8. The method of claim 1, wherein the progesterone is administered within one hour prior to the subject retiring.

9. The method of claim 1, wherein the method comprises once daily administration of progesterone over a period of time of at least 7 days.

10. The method of claim 1, wherein the method comprises once daily administration of progesterone over a period of time of at least 30 days.

11. The method of claim 1, wherein the therapeutically effective amount of progesterone is from 200 mg to 500 mg daily.

12. The method of claim 11, wherein the therapeutically effective amount of progesterone is from 300 mg to 400 mg daily.

13. The method of claim 1, wherein the progesterone is administered orally.

14. The method of claim 1, wherein the progesterone is provided in a pharmaceutical composition in the form of a soft capsule comprising micronized progesterone solubilized in an edible oil.

15. The method of claim 14, wherein the edible oil is selected from the group consisting of peanut, sunflower, olive, almond, sesame and colza oils.

16. The method of claim 1, wherein the improved sleep quality further comprises one or more of a decrease in wake time, increase in REM sleep, increase in sleep maintenance, increase in sleep efficiency, decrease in sleep latency, and/or normalization of distribution of slow-wave and REM stages during the sleep period.

* * * * *